United States Patent [19]

Grollier

[11] Patent Number: 4,540,507
[45] Date of Patent: Sep. 10, 1985

[54] CLEANING PRODUCT FOR THE HAIR AND SKIN, BASED ON ACYLISETHIONATES, CATIONIC POLYMERS AND SALTS OF FATTY ACID/POLYPEPTIDE CONDENSATES

[75] Inventor: Jean F. Grollier, Paris, France

[73] Assignee: L'Oreal, Paris, France

[21] Appl. No.: 461,525

[22] Filed: Jan. 27, 1983

[30] Foreign Application Priority Data

Jan. 29, 1982 [LU] Luxembourg ............... 83911

[51] Int. Cl.³ ............... A61K 7/06; C11D 7/34
[52] U.S. Cl. ............... 252/174.23; 252/542; 252/557; 252/DIG. 2; 252/DIG. 5; 252/DIG. 13; 424/70; 424/71
[58] Field of Search ............... 252/DIG. 2, DIG. 13, 252/DIG. 5, 557, 542, 174.23; 424/70, 71

[56] References Cited

U.S. PATENT DOCUMENTS 3,980,769 9/1976 Ghilardi et al. .
4,223,009 9/1980 Chakrabrati ............... 424/71
4,265,782 5/1981 Armstrong et al. ............... 252/174.16

FOREIGN PATENT DOCUMENTS 1333819 9/1973 United Kingdom .

OTHER PUBLICATIONS

Maypoons for Cosmetics—Maywood Chemical Works, Maywood, N.J.

Primary Examiner—John E. Kittle
Assistant Examiner—Mukund J. Shah
Attorney, Agent, or Firm—Cushman, Darby & Cushman

[57] ABSTRACT

A cleaning composition for the hair and/or skin which comprises a cosmetically acceptable medium containing (a) at least one surface-active agent of the formula:

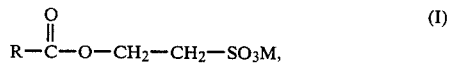

in which R denotes a linear or branched alkyl group and M denotes an alkali metal or alkaline earth metal or an amine, (b) at least one cationic polymer which is a quaternized or unquaternized vinylpyrrolidone/dialkylaminoalkyl acrylate or methacrylate copolymer, and (c) at least one salt of a fatty acid/polypeptide condensate.

16 Claims, No Drawings

CLEANING PRODUCT FOR THE HAIR AND SKIN, BASED ON ACYLISETHIONATES, CATIONIC POLYMERS AND SALTS OF FATTY ACID/POLYPEPTIDE CONDENSATES

The present invention relates to cleaning products for the hair and/or skin, based on acylisethionates, cationic polymers and salts of fatty acid/polypeptide condensates, and also to the process in which the compositions are used.

For many years, cleaning products for the hair and/or skin have been formulated from surface-active agents which can be anionic, amphoteric, non-ionic or cationic and which are used by themselves or in a mixture. The overall use concentration is generally between 5 and 20%.

Furthermore, it has already been recommended, with a view to improving the cosmetic properties of these compositions, to add cationic compounds, and in particular cationic polymers, thereto.

As is known, cationic polymers improve the softness by depositing on the hair, and the hair is the easier to comb out, the greater the amount of polymers deposited. This deposit is the larger, the more sensitised the fibre, that is to say the greater the number of sulphonic groups it contains which are capable of fixing the cationic charges of the polymer.

We have found that the deposits of these polymers are substantially larger if non-ionic media rather than anionic media are used. This difference in efficacy is partly due to the interactions between the cationic polymer and the anionic surface-active agent, which partially inhibits the deposition of polymer.

However, anionic surface-active agents have better detergency properties than non-ionic surface-active agents, so that it has seemed desirable to be able to retain these properties while at the same time improving the softness of the hair and/or skin to the touch and the comb-out of the hair.

We have found, in particular, that the interaction between the cationic polymer and the anionic surface-active agent is particularly strong for surface-active agents of high polarity and in particular for sulphated or sulphonated anionic surface-active agents.

It has now been discovered that, by using a combination of a surface-active agent from the family of the acylisethionates, a cationic polymer chosen from amongst vinylpyrrolidone/dialkylaminoalkyl acrylate or methacrylate copolymers and a salt of a fatty acid/polypeptide condensate, a homogeneous composition is obtained which improves the feel of the skin or hair, imparts softness to the skin and has a very good degree of harmlessness towards the skin.

The invention thus relates to a cleaning composition for the hair and/or skin which contains the various constituents mentioned.

The invention also relates to a process for cleaning the hair and skin, which essentially uses a composition of this type.

Further objects of the invention will become apparent on reading the description and the examples which follow.

The cleaning composition for the hair and/or skin, according to the invention, comprises, a cosmetically acceptable medium containing at least one surface-active agent of the formula:

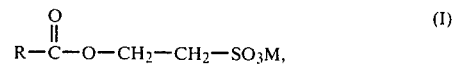

in which R denotes a linear or branched alkyl group and M denotes an alkali metal or alkaline earth metal or an amine, a vinylpyrrolidone/dialkylaminoalkyl acrylate or methacrylate copolymer and a salt of a fatty acid/polypeptide condensate.

In the abovementioned formula (I), R preferably denotes an alkyl group having between 8 and 18 carbon atoms; the groups which are particularly preferred consist of a group having 12 to 14 carbon atoms or a group derived from copra oil. M preferably denotes sodium, potassium or magnesium, sodium being particularly preferred.

The vinylpyrrolidone/dialkylaminoalkyl acrylate or methacrylate copolymers (quaternised or unquaternised) correspond, in particular, to the formula

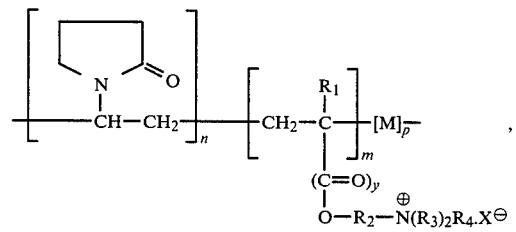

in which n is between 20 and 99 and preferably between 40 and 90 mol% and m is between 1 and 80 and preferably between 5 and 40 mol%; p represents 0 to 50 mol% and $n+m+p=100$; $R_1$ represents H or $CH_3$; y denotes 0 or 1; $R_2$ is $-CH_2-CHOH-CH_2-$ or $C_xH_{2x}$, in which $x=2$ to 18; $R_3$ represents $CH_3$, $C_2H_5$ or

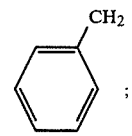

$R_4$ denotes $CH_3$ or $C_2H_5$; $X^-$ is chosen from amongst Cl, Br, I, 1/2 $SO_4$, $HSO_4$ and $CH_3SO_3$; and M is a monomeric unit resulting from heteropolymerisation using a selected copolymerisable vinyl monomer. The polymers can be prepared by the process described in French Pat. Nos. 2,077,143 and 2,393,573.

The preferred copolymers have a molecular weight of between about 100,000 and 1,000,000, such as the commercial products "copolymer 845", "Gafquat 734" and "Gafquat 755" from the "GAF CORPORATION" in New York.

As salts of fatty acid/polypeptide condensates there may be mentioned, in particular, the triethanolamine salts of a lauric acid/keratin polypeptide condensate and the potassium salts of a coconut fatty acid/collagen polypeptide condensate, sold under the name Lamepon S by GRUNAU.

The surface-active agent, the cationic polymer and the salt of a fatty acid/polypeptide condensate are present in a cosmetically acceptable medium, which can be liquid or solid.

The cationic polymer used according to the invention is preferably present in proportions of 0.05 to 5% by weight, relative to the total weight of the composition, and in particular of between 0.2 and 1.5% of active ingredient, and the surface-active agent of the formula (I) is preferably used in proportions of 5 to 30% by weight and in particular of 5 to 15% for the liquid forms, it being possible for the proportions to range up to 90% for the solid forms. The salt of a fatty acid/polypeptide condensate is present in sufficient proportions to give a homogeneous composition, and preferably in proportions of the order of 2 to 5% by weight of active ingredient.

The preferred ratio of the cationic polymer, expressed as active ingredient, to the surface-active agent of the formula (I) is between 0.01 and 0.3.

If the compositions are intended to be used for cleaning the skin, they can be presented in the form of a cleansing cream, a milk, a gel, a make-up remover lotion or a thickened lotion. If the compositions are intended for washing the hair, they can be presented in the form of a shampoo, or a rinse-off treating product to be applied before or after shampooing or before or after other hair treatments.

If the compositions are in liquid form, they can contain water, a cosmetically acceptable solvent such as a monoalcohol, a polyalcohol, a glycol ether or their esters, and also mixtures thereof.

These compositions can contain various cosmetic adjuvants such as perfumes, dyestuffs, preservatives, sequestering agents, thickeners, antioxidants, sun filters and foam stabilisers, and also any other adjuvant chosen according to the application envisaged. The pH of the compositions can be between 5 and 8.5.

The compositions which are more particularly preferred are the liquid compositions, and they have a pH substantially in the region of neutrality and preferably of between 6 and 8.

An advantageous embodiment of the invention consists in introducing thickeners into the compositions according to the invention, these thickeners making it possible to obtain a good viscosity and to keep the surface-active agent of the formula (I) in suspension in an unctuous form. The thickeners can be chosen, in particular, from amongst vegetable thickeners such as gum arabic, karaya gum, gum tragacanth, guar gum, carob gum, tara gum, pectins, alginates, carragheenates and agar-agar; cellulose derivatives such as methylcellulose, hydroxymethylcellulose, hydroxyethylcellulose, hydroxypropylcellulose and hydroxypropylmethylcellulose; synthetic polymers such as sodium polyacrylate, polyvinyl alcohol and carboxylic polymers derived from acrylic acid, such as carbopols; and polyethylene glycol esters and polyethylene glycol ethers.

These compositions can also contain non-ionic surface-active agents, used by themselves or in a mixture; the following may be mentioned in particular; polyoxyethyleneated, polyoxypropyleneated, or polyglycerolated alcohols, alkylphenols and fatty acids having a linear fatty chain containing 8 to 18 carbon atoms and most frequently containing 2 to 30 mols of ethylene oxide. There may also be mentioned ethylene oxide/propylene oxide copolymers, condensates of ethylene oxide and propylene oxide with fatty alcohols, polyoxyethyleneated fatty amides, polyoxyethyleneated fatty amines, ethanolamides, fatty acid esters of glycol, oxyethyleneated or non-oxyethyleneated fatty acid esters of sorbitan, fatty acid esters of sucrose, fatty acid esters of polyethylene glycols, phosphoric acid triesters and fatty acid esters of glucose derivatives.

Other compounds included in this class are: products resulting from the condensation of a monoalcohol, an α-diol, an alkylphenol, an amide or a diglycolamide with glycidol, such as:

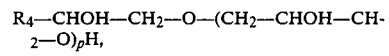

in which $R_4$ denotes an aliphatic, cycloaliphatic or arylaliphatic radical preferably having between 7 and 21 carbon atoms, and mixtures thereof, it being possible for the aliphatic chains to contain ether, thioether or hydroxymethylene groups, and in which p is between 1 and 10 inclusive, such as the products described in French Patent No. 2,091,516; compounds corresponding to the formula:

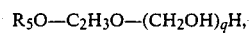

in which $R_5$ denotes an alkyl, alkenyl or alkylaryl radical and q has a statistical value of between 1 and 10 inclusive, such as the compounds described in French Patent No. 1,477,048; and compounds corresponding to the formula:

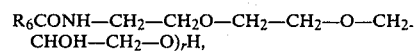

in which $R_6$ denotes a linear or branched, saturated or unsaturated aliphatic radical, or a mixture of such radicals, which can optionally contain one or more hydroxyl groups, which has between 8 and 30 carbon atoms and which is of natural or synthetic origin, and r represents an integer or decimal number from 1 to 5 and denotes the average degree of condensation, such as the compounds described in French Patent No. 2,328,763.

Amphoteric surface-active agents can also be used, and there may be mentioned, more particularly, alkylaminomonopropionates and -dipropionates, betaines such as N-alkylbetaines, N-alkylsulphobetaines and N-alkylamidobetaines, cycloimidinium compounds such as alkylimidazolines, and asparagine derivatives.

If the compositions are in solid form, they contain, in addition to the surface-active agent of the formula (I) the cationic polymer and the salt of a fatty acid/polypeptide condensate, thickeners other than polyethylene glycol ethers, superfatting agents such as lecithin, binders such as polyethylene glycols, plasticisers, foam stabilisers, sequestering agents or antioxidants.

The process for cleaning the hair and skin, according to the invention, consists essentially in applying a composition such as defined above to the wet hair and/or wet skin, and, after application and an interval of a few minutes, in rinsing with water.

The combination according to the present invention can also be formed on the hair or skin by applying the acylisethionate of the formula (I) in a first step and the cationic polymer in a second step, by means of compositions corresponding to the above definitions.

The examples which follow are intended to illustrate the invention without thereby implying a limitation.

EXAMPLE 1

The following composition is prepared:

| | |
|---|---:|
| Sodium acylisethionate (acyl is a residue of copra fatty acid sold under the name FENOPON AC 78 by GAF | 57 g |

-continued

| | |
|---|---|
| Potassium salt of a coconut fatty acid/collagen polypeptide condensate, sold under the name Lamepon S by GRUNAU | 2 g (active ingredient) |
| White paraffin wax | 29 g |
| Rice starch | 2.4 g |
| Quaternary vinylpyrrolidone copolymer having a molecular weight of 1,000,000, sold by General Aniline under the name Gafquat 755 | 1.5 g (active ingredient) |
| Titanium dioxide | 0.1 g |
| Water | 8 g |

This composition is in the form of a dermatological cake, which imparts softness to the skin during washing.

EXAMPLE 2

The following composition is prepared:

| | |
|---|---|
| Sodium acylisethionate (acyl is a residue of copra fatty acid sold under the name FENOPON AC 78 by GAF | 70.30 g |
| Potassium salt of a coconut fatty acid/collagen polypeptide condensate, sold under the name Lamepon S by GRUNAU | 4.5 g (active ingredient) |
| White paraffin wax | 13.50 g |
| Rice starch | 1 g |
| Quaternary vinylpyrrolidone copolymer having a molecular weight of 1,000,000 sold by General Aniline under the name Gafquat 755 | 0.5 g (active ingredient) |
| Titanium dioxide | 0.2 g |
| Water | 10 g |

This gives a product in the form of a solid cake, which imparts a soft feel to the skin.

EXAMPLES 3 AND 4

The following compositions are prepared:

| | Example 3 | Example 4 |
|---|---|---|
| Sodium acylisethionate (acyl is a residue of copra fatty acid) sold under the name FENOPON AC 78 by GAF | 10 g | 10 g |
| Potassium salt of a coconut fatty acid/ collagen polypeptide condensate, sold under the name LAMEPON S by GRUNAU | 2 g (active ingredient) | 5 g (active ingredient) |
| Quaternary vinylpyrrolidone copolymer having a molecular weight of 1,000,000, sold by General Aniline under the name Gafquat 755 | 0.5 g (active ingredient) | 0.25 g (active ingredient) |
| Glycerol | 2 g | 2 g |
| Ethylene glycol distearate | 2 g | 2 g |
| Copra diethanolamide | 3 g | 5 g |
| Methyl p-hydroxybenzoate | 0.3 g | 0.3 g |
| Water q.s. | 100 g | 100 g |

The pH is equal to 7.

These compositions are liquid soaps, which impart characteristics of softness to the touch when the hair and skin are washed with these soaps.

I claim:

1. A cleaning composition for the hair and skin consisting essentially of, in combination, in a cosmetically acceptable medium,
   (a) at least one surface-active agent of the formula:

$$R-\overset{O}{\underset{\|}{C}}-O-CH_2-CH_2-SO_3M \quad (I)$$

wherein R denotes a linear or branched alkyl group and M denotes an alkali metal or alkaline earth metal or an amine,
   (b) at least one cationic polymer selected from a quaternized or non-quaternized vinylpyrrolidone/-dialkylaminoalkyl acrylate or methacrylate copolymer, and
   (c) at least one salt of a fatty acid/polypeptide condensate.

2. A composition according to claim 1, wherein, in the formula (I), R denotes a group having 8 to 18 carbon atoms.

3. A composition according to claim 1 wherein M is selected from sodium, potassium or magnesium.

4. a composition according to claim 1 wherein R is selected fron an alkyl group having 12 to 14 carbon atoms or a group derived from copra oil.

5. A composition according to claim 1 wherein the cationic polymer (b) is present in an amount of 0.05 to 5% by weight, relative to the total weight of the composition.

6. A composition according to claim 5 wherein the cationic polymer (b) is present in an amount of 0.2 to 1.5% by weight, relative to the total weight of the composition.

7. A composition according to claim 1 wherein the surface-active agent of the formula (I) is present in an amount of 5 to 30% by weight when the composition is in the form of a liquid and of up to 90% by weight when the composition is in the form of a solid.

8. A composition according to claim 1 wherein the salt of a fatty acid/polypeptide condensate (c) is selected from the triethanolamine salts of a lauric acid/keratin polypeptide condensate and the potassium salts of a copra fatty acid/collagen polypeptide condensate.

9. A composition according to claim 1 wherein the salt of a fatty acid/polypeptide condensate (c) is present in an amount of 2 to 5% by weight.

10. A composition according to claim 1 wherein the ratio of the cationic polymer (b) to the surface-active agent of the formula (I) is from 0.01 to 0.3:1.

11. A composition according to claim 1 wherein the composition is liquid and the cosmetically acceptable medium is selected from water, a solvent or a mixture thereof.

12. A composition according to claim 1 which contains a thickener selected from vegetable thickeners, cellulose derivatives, synthetic polymers other than cationic polymers, polyethylene glycol esters or polyethylene glycol ethers.

13. A composition, suitable for cleaning the skin, according to claim 1 selected from a cleansing cream, a milk, a gel, a make-up remover lotion, a thickened lotion or a dermatological cake.

14. A composition, suitable for washing the hair, according to claim 1 selected from a shampoo or a rinse-off product applied before or after shampooing.

15. A composition according to claim 1 which is in the form of a liquid and in which the surface-active agent of the formula (I) is present in an amount of 5 to 15% by weight.

16. Process for cleaning the hair or skin, which process comprises applying thereto at least one composition as defined in claim 1.

* * * * *